United States Patent [19]

Ryder et al.

[11] Patent Number: 4,743,738

[45] Date of Patent: May 10, 1988

[54] CONTACT LENS DISINFECTOR

[75] Inventors: Francis E. Ryder, Arab; Rowland W. Kanner, Guntersville; Fred E. Williams, Arab, all of Ala.

[73] Assignee: Ryder International Corporation, Arab, Ala.

[21] Appl. No.: 12,432

[22] Filed: Feb. 9, 1987

[51] Int. Cl.⁴ .............................................. H05B 3/14
[52] U.S. Cl. .................................. 219/521; 219/505; 219/386; 422/307
[58] Field of Search ............... 219/385, 386, 387, 521, 219/438, 439, 430, 504, 505, 441, 442, 432, 200, 201; 422/307; 439/134, 149

[56] References Cited

U.S. PATENT DOCUMENTS

| | | | |
|---|---|---|---|
| 4,060,297 | 11/1977 | Marshall | 439/149 |
| 4,165,359 | 8/1979 | Thomas | 219/521 |
| 4,258,970 | 3/1981 | Bourdon | 439/149 |
| 4,307,289 | 12/1981 | Thomas | 219/521 |
| 4,341,948 | 7/1982 | Sundström | 219/521 |
| 4,472,623 | 9/1984 | Futter | 219/505 |

FOREIGN PATENT DOCUMENTS 2416492 10/1979 France ..................... 219/201
56-94325 7/1981 Japan ...................... 219/521

Primary Examiner—Clifford C. Shaw
Assistant Examiner—Teresa J. Walberg
Attorney, Agent, or Firm—Trexler, Bushnell, Giangiorgi & Blackstone, Ltd.

[57] ABSTRACT

A contact lens disinfecting apparatus includes a housing defining a pair of receptacles for receiving a pair of contact lenses and a quantity of liquid therein, a heater responsive to a predetermined electrical current for producing heat, the heater being configured and positioned in the housing for radiating heat to the receptacles for disinfecting contact lenses therein, energizing-and-timing circuit also mounted in the housing for controlling the application of the predetermined electrical current to the heater, an AC connector coupled with the housing for coupling with mating AC connector for energizing the circuit, and a shield interposed between the receptacle on the one hand and both the circuit and the heater on the other hand and providing collecting and draining for respectively collecting and directing outwardly of the housing any liquid which may escape or otherwise exit beneath the receptacle, so as to prevent the liquid from contacting the heater or the electrical circuit.

11 Claims, 3 Drawing Sheets

U.S. Patent    May 10, 1988    Sheet 3 of 3    4,743,738

CONTACT LENS DISINFECTOR

BACKGROUND OF THE INVENTION

This invention is directed generally to the field of contact lens disinfecting systems and more particularly to improvements in a contact lens disinfecting apparatus of the type including lens receptacles, a heating element and an energizing-and-timing circuit contained within a housing adapted to be directly coupled with a conventional AC outlet or socket for an automatic, timed disinfecting cycle.

Soft and extended wear type of contact lenses are widely used. These types of contact lenses are manufactured of a hydrophilic plastic porous material which can be formed to the desired lens curvature. This material, as indicated absorbs water or moisture so as to become relatively soft and pliable, and hence relatively comfortable to wear.

While the older hard type of contact lenses require periodic cleaning and/or disinfecting, the cleaning and especially the disinfecting of these soft and extended wear contact lenses is recommended more frequently. This frequency is largely due to the porous nature of the plastic materials utilized in the construction of these types of contact lenses. This porous material tends to absorb bodily fluids, which include a number of materials in solution, during wear. These materials in solution may come out of solution during wear and build up over time in the pores of the lens, resulting in clouding and discoloration of the lens. Accordingly, thorough cleaning is necessary from time to time to remove these materials from the pores of the lens. Moreover, these pores also provide areas of bacterial growth, and hence fairly frequent disinfecting of the lenses is also recommended. Several disinfecting methods have been developed and employed with success in connection with the soft and extended wear contact lenses. One particularly successful and widely used method involves placing the lenses in a saline or other disinfecting solution and heating the solution to a temperature sufficient to destroy any bacteria which may be present.

This disinfecting method generally employs a case or receptacle containing a quantity of the disinfecting or saline solution, which case or receptacle is placed in contact with a suitable heating element or unit. Thus, direct application of heat is obtained from the heating element or unit to the case and solution contained therein.

A number of devices have heretofore been proposed in easy to use unitary and/or modular forms for simply and readily carrying out this process. One such disinfecting unit is shown for example in U.S. Pat. No. 4,529,868 to Bowen, et al. Another such unit is shown in the co-pending application of Ryder et al, Ser. No. 734,410, filed May 14, 1985 now U.S. Pat. No. 4,659,911. While the foregoing types of disinfecting units have enjoyed some degree of success, there is nonetheless room for further improvement.

The present invention pertains to a disinfecting unit or apparatus which utilizes a single, compact and easy to use plug-in type of unit. This unit comprises a combined energizing-and-timer circuit, heating module and receptacles for contact lenses and a quantity of saline or other disinfecting solution. Importantly, the disinfecting unit or apparatus of the invention provides novel shielding and drainage components for collecting and draining outwardly of the unit any moisture which may develop around or adjacent the receptacles in use, as might occur for example due to cracking of the receptacles or otherwise. The preferred form of the invention which will be illustrated and described herein also provides additional shielding for the circuit components, as well as a novel removable cover member for covering an AC connector portion of the unit when not in use.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in the several figures of which like reference numerals identify like elements, and in which:

DETAILED DESCRIPTION OF THE ILLUSTRATED EMBODIMENT

Figure 1:
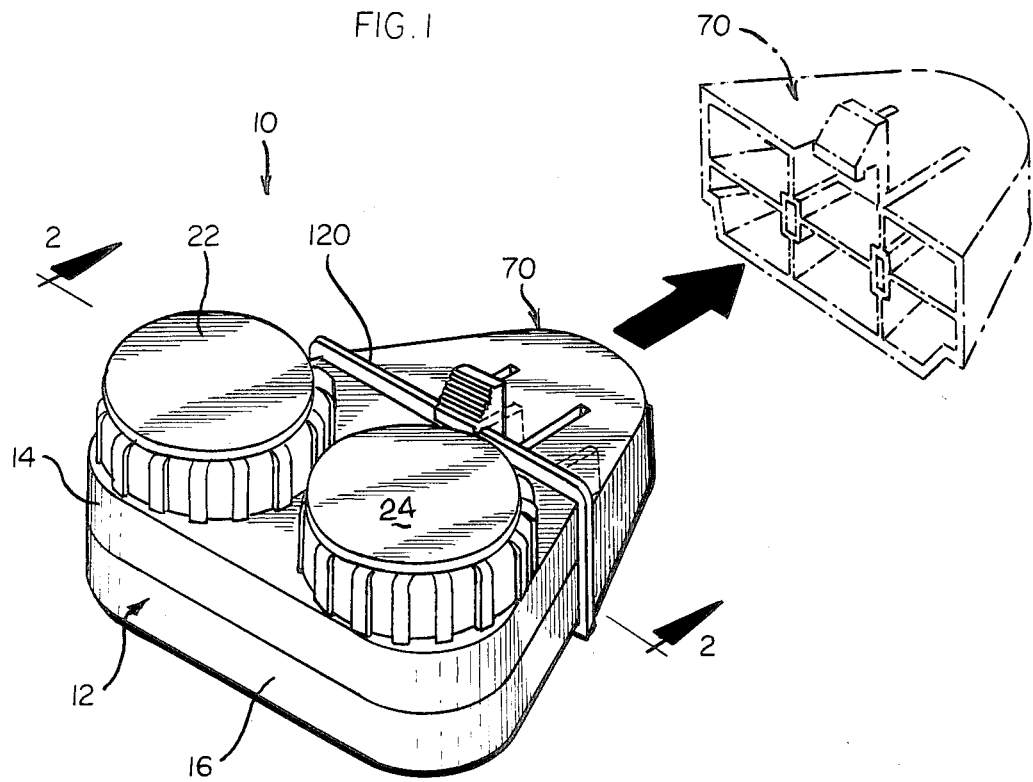
FIG. 1 is a perspective view of the contact lens disinfecting apparatus in accordance with the invention, illustrating further in phantom line the removable nature of the cover associated with the AC connector portion of the apparatus.
Figure 2:
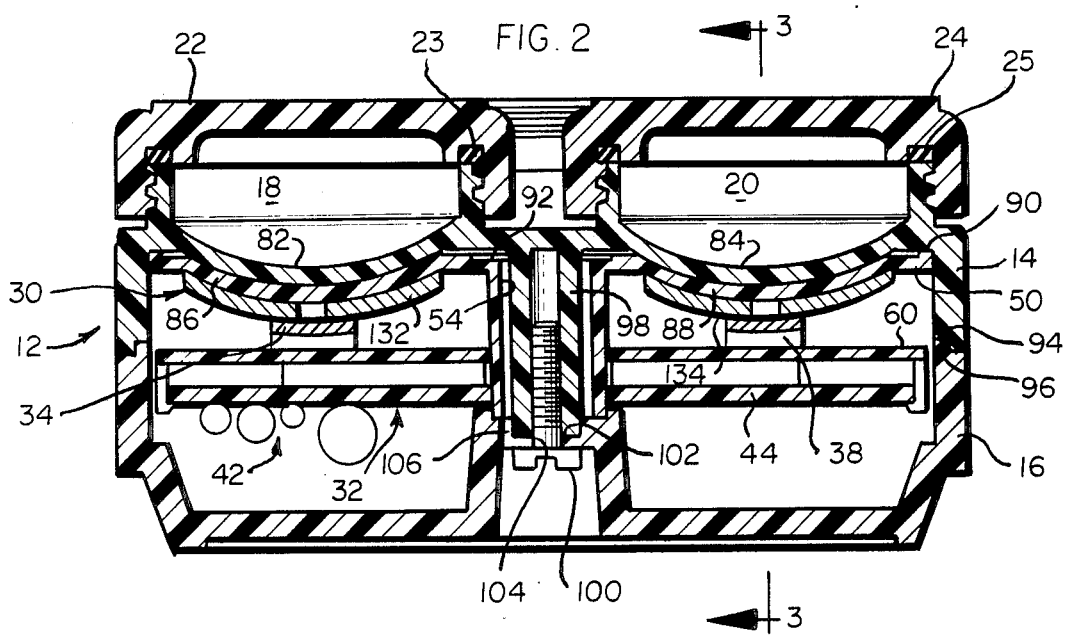
FIG. 2 is an enlarged sectional view taken generally in the plane of the line 2—2 of FIG. 1.

Referring to the drawings, and initially to FIGS. 1 and 2, a novel and improved contact lens disinfecting apparatus in accordance with the invention is designated generally by the reference numeral 10. Generally speaking, the apparatus 10 includes a housing 12 which is comprised of an upper housing portion 14 and a lower housing portion 16. Defined in the upper housing portion 14 are a pair of receptacles 18, 20 for receiving respective ones of a pair of contact lenses (not shown) therein, together with a quantity of saline or other disinfecting solution (not shown). Preferably, the receptacles 18, 20 are provided with a pair of threadably engageable and disengageable covers or cap members 22, 24. These caps are further provided with seals in the form of flat, annular elastomeric rings 23, 25 seated in complementary annular recesses. The rings 23, 25 are positioned to sealingly abut upper edges of the respective receptacles 18, 20.

Figure 3:
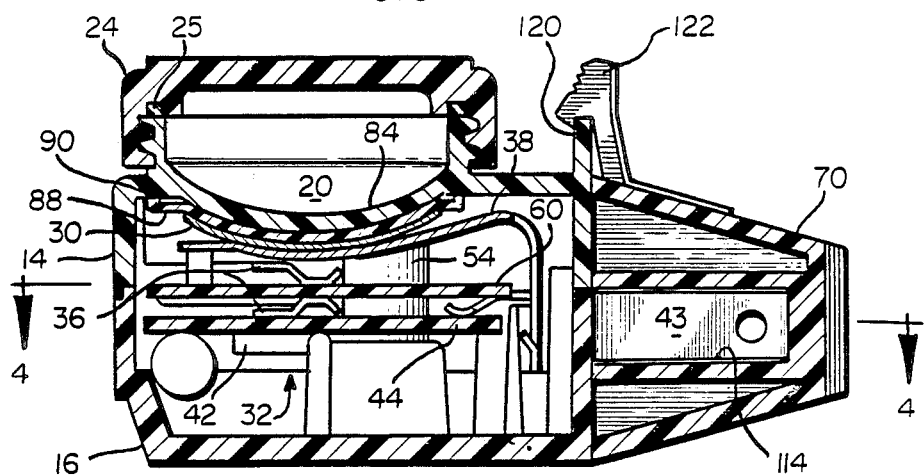
FIG. 3 is a sectional view taken generally in the plane of the line 3—3 of FIG. 2.
Figure 4:
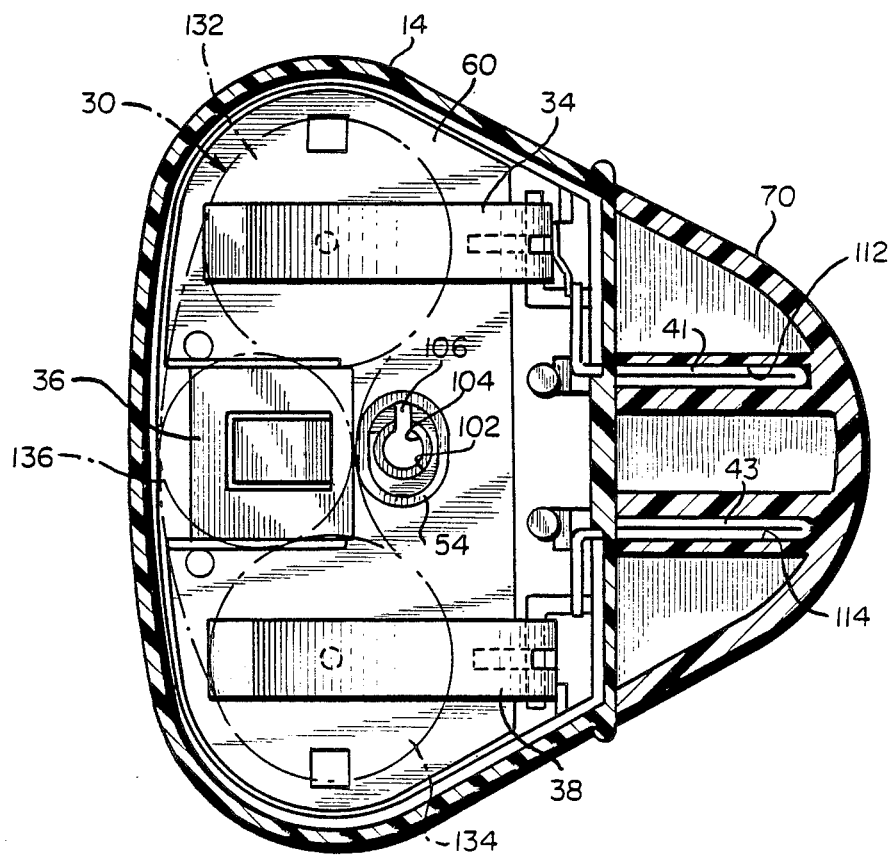
FIG. 4 is a sectional view taken generally in the plane of the line 4—4 of FIG. 3.
Figure 5:
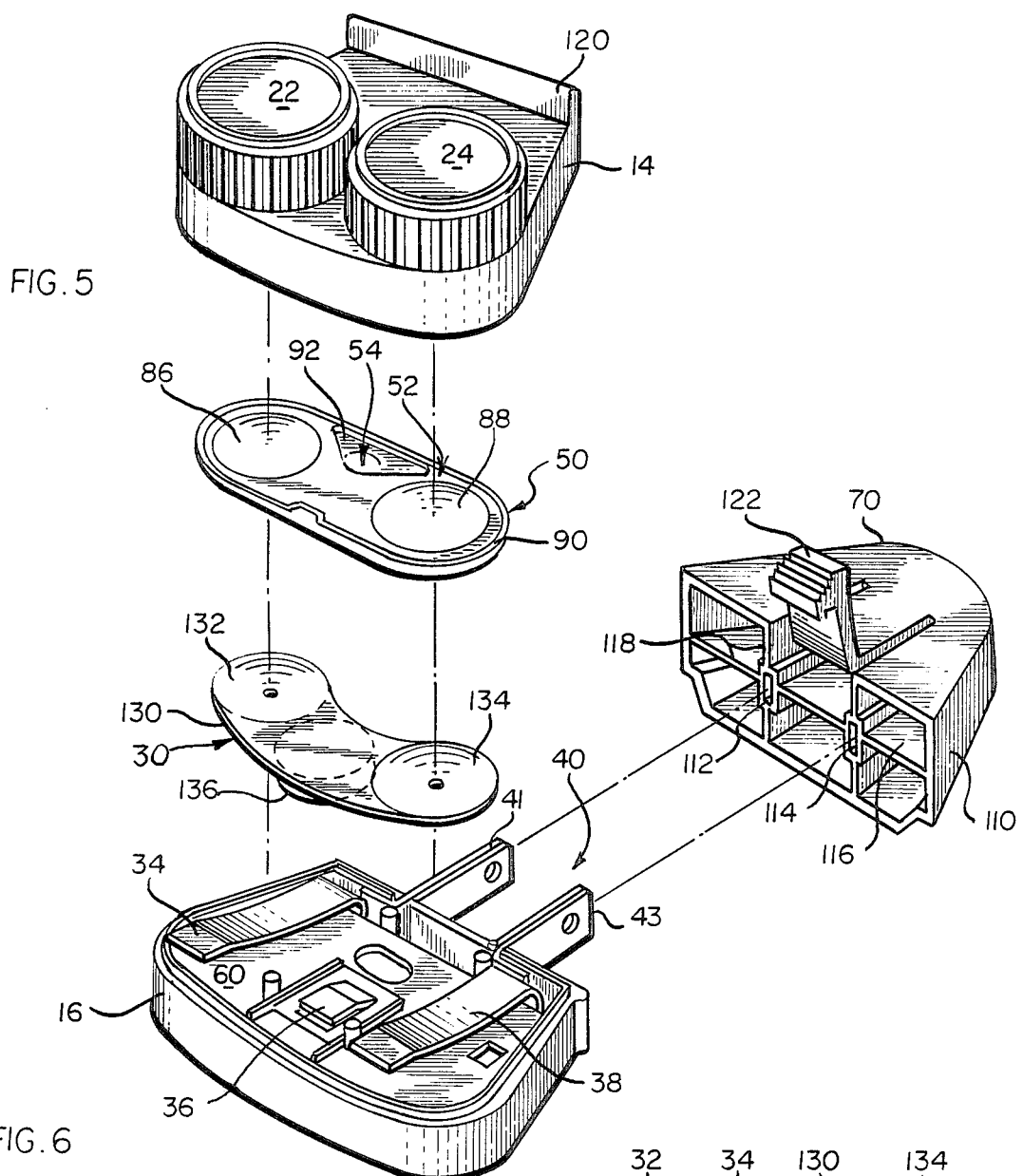
FIG. 5 is an exploded perspective view illustrating further a number of the component parts of the apparatus of the invention and their assembly.

Referring now also to FIGS. 3 through 5, heater means 30 are provided, and are responsive to a predetermined electrical current for producing heat. The heater means 30 are configured and positioned in the housing 12 for radiating heat to the receptacles 18, 20 for disinfecting contact lenses therein. An energizing-and-timer circuit 32 (shown in schematic form in FIG. 6) is also mounted in the housing 12 and is electrically coupled with the heater means 30 for supplying the electrical current to the heating means 30 for energizing the same over predetermined time intervals, as will be explained more fully hereinbelow.

The electrical connections between the AC connector 40, the circuit 32 and the heater means 30 are accomplished by respective electrical contactors or contact elements 34, 36, 38 as will be more fully described hereinbelow.

Advantageously, the apparatus of the invention is assembled as a self-contained unit, whereby electrical power from a suitable external power source is received by way of electrical connector means 40 which are mounted to the housing 12 for connection with mating electrical connector means of a suitable power source. In the illustrated embodiment, the connector means 40 comprise AC blade-type connector members 41, 43 for coupling with a mating AC socket or receptacle, the circuit 32 being operable by either 120 volt AC household current or 240 volt AC European household current.

The circuit means 32 comprise a number of circuit components 42, which are somewhat diagrammatically indicated in FIGS. 2 and 3, mounted to a printed circuit (PC) board 44, which is in turn mounted in the lower housing half or part 16. In accordance with an important feature of the invention, a shielding or shield means or member 50 (best viewed in FIG. 5) is interposed between the receptacles 18, 20 and the electrical circuit 32 and preferably between the receptacles and the heating means 30. This shield 50 includes a collecting means or portion 52 and a drain means or portion 54 for respectively collecting and directing outwardly of the housing 12 any liquid which may escape the receptacles or receptacle means 18, 20, so as to prevent such liquid from contacting any part of the electrical circuit 32, including the heating means 30, which, as will be seen presently, is electrically coupled with the AC connector means 40 and circuit 32. In accordance with the preferred form of the invention illustrated, an additional shield member 60 is additionally interposed overlying the circuit means 32, and in particular, overlying the back or rear surface of the printed circuit board 44, for additionally protecting the same. This latter shield 60 protects the printed circuit side of the board 44 from any contact with heating means 30, except by way of contacts 34, 36 and 38.

In accordance with another aspect of the invention, there is further provided a cover means or member 70 which is removably engageable with the housing 12, as indicated in phantom line in FIG. 1, for selectively covering the outwardly extending portions of the connector means or AC blade-type connector means when the apparatus or unit 10 is not in use.

Referring now to the drawings in additional detail, and in particular to FIGS. 2 through 5, further details of the foregoing parts and their cooperation in the unit or apparatus of the invention will now be described in further detail. The receptacles or receptacle means 18, 20 will be seen to comprise generally circular, dished side-by-side identical receptacles or depressions. Preferably, dished bottom portions 82, 84 of these receptacles extend downwardly in a generally concave fashion as best viewed in FIGS. 2 and 3. In this regard, the directions up and down will be understood to be with respect to the normal orientation of the apparatus when in use, this orientation being that generally illustrated in FIGS. 1 through 3 and FIG. 5 of the drawings. Cooperatively, the shield means or member 50 comprises a generally oblong member of a relatively thin material, which defines a pair of complementary dished portions 86, 88 for underlying the dished bottoms 82, 84 of the receptacles 18 and 20. The collecting portion or means 52 of the shield 50 is further defined by an upstanding peripheral rim 90 which encircles or surrounds the entire circumference of the shield 50. The drain means 54 comprises an elongate tubular depending member which is in communication both with the collecting portion or volume 52 defined within the rim 90 and with the exterior of the housing 12 as will be more fully described presently. In the illustrated embodiment, an additional depression or recessed area 92 is provided generally surrounding the inlet of this tubular drain portion 54 from the collector portion 52.

In order to effect assembly of the upper and lower housing halves or parts 14, 16, similar, peripheral, interlocking inner and outer lip portions 94, 96 as well as a threadably engaged assembly post 98 and threaded fastener 100 are provided. The interlocking inner and outer lip portions 94 and 96 generally cooperate to position the two housing portions in the proper orientation and alignment. The post 98 is formed depending from an inner surface of the upper housing half or member 14 in the illustrated embodiment. Cooperatively, the lower housing member or half 16 is provided with a complementary recessed abutment surface 102 for positioning and receiving a lower end of the post 98. A through aperture 104 is provided generally centrally located in surface 102 for receiving the threaded fastener 100 therethrough for threaded engagement with complementary threads formed interiorally of the post 98.

In order to assure drainage of any liquid from the collector portion 52 of the shield 50, the tubular drain means or member 54 is of greater transverse dimension than the post 98. In this regard, the post 98 is preferably cylindrical in form, while the drainage tube 54 is preferably generally elliptical or oval in form, thus defining a major transverse inner dimension somewhat greater than the outer diameter of the post 98 to permit the flow of liquid therearound. To accommodate the flow of liquid from the drainage tube 54 outwardly of the housing, the through aperture 104 is preferably irregularly shaped, such that the through opening 104 extends laterally or radially outwardly of the head if the screw 100, at least in part, to accommodate liquid flow therearound. In the illustrated embodiment, the through aperture 104 is keyhole-shaped as best viewed in FIG. 4. That is, the outwardly extending portion 106 of keyhole-shaped opening or through aperture 104 is in direct communication with the lower open end of the tubular drain member or portion 54 to permit exit of liquid therethrough.

As previously mentioned, the means 40 comprise AC blade-type connectors 41, 43. Accordingly, to accommodate the same, the cover member or means 70 includes an outer housing or shield portion 110 within which are formed a pair of complementary sheath-like members or portions 112, 114 for slidably engaging over and covering the blades 41, 43. Preferably these sheath-like members 112 and 114 are held in substantially symmetrically centered locations within the housing or cover 110 by transversely extending integrally formed rib-like support members 116, 118. In order to releasably engage the cover 70 with the housing 12, an outwardly projecting lip portion or member 120 is formed on the housing 12 and preferably on the upper housing half or part 14. Cooperatively, the cover 70 includes a manually releasable, resilient, hook-like clip or clasp portion 122 configured for resilient, releasable engagement with the lip 120.

Turning now to the heating means or element 30 and associated energizing-and-timing circuit 32, additional details of these elements will be described with reference being directed primarily to FIGS. 5 and 6. The heating means 30 will be seen to comprise a generally oblong heat sink member 130 which is generally dished as indicated at 132, 134 in a complementary fashion for underlying the respective dished portions of the shield 50 and of the receptacles 18 and 20 described hereinabove. These dished portions 132 and 134 are formed on the relatively thin, and preferably metallic, electrically conductive heat sink member which is curved somewhat to extend about the downwardly descending drain member or tube 54. A heating element 136 is mounted to the underside of the heat sink 130 generally midway between the dished portions 132 and 134. Preferably, this heating element is both electrically and thermally coupled with the heat sink 130 by means of a conductive cement material.

Electrical contacts with the exposed side of heating element 136, as well as with the undersides of the dished portions 132 and 134 of heat sink 130 are made by the respective contactors 36, 34 and 38. which it will be noted are resilient, spring-like or leaf-type contactors. The contactors 34 and 38 are further provided with clip-like ends for mechanical interconnection with the lower housing 16 and with the printed circuit board 44, and for electrical contact with the desired point in the circuit on the PC board. The contactor 36 is bi-ended, being mounted in clip-like fashion to shield or plate member 60 and having oppositely extending spring-like leaf contacts for electrical contact respectively with the desired point in the circuit or PC board 44 on the one side and with the heating element 136 on the other side.

Figure 6:
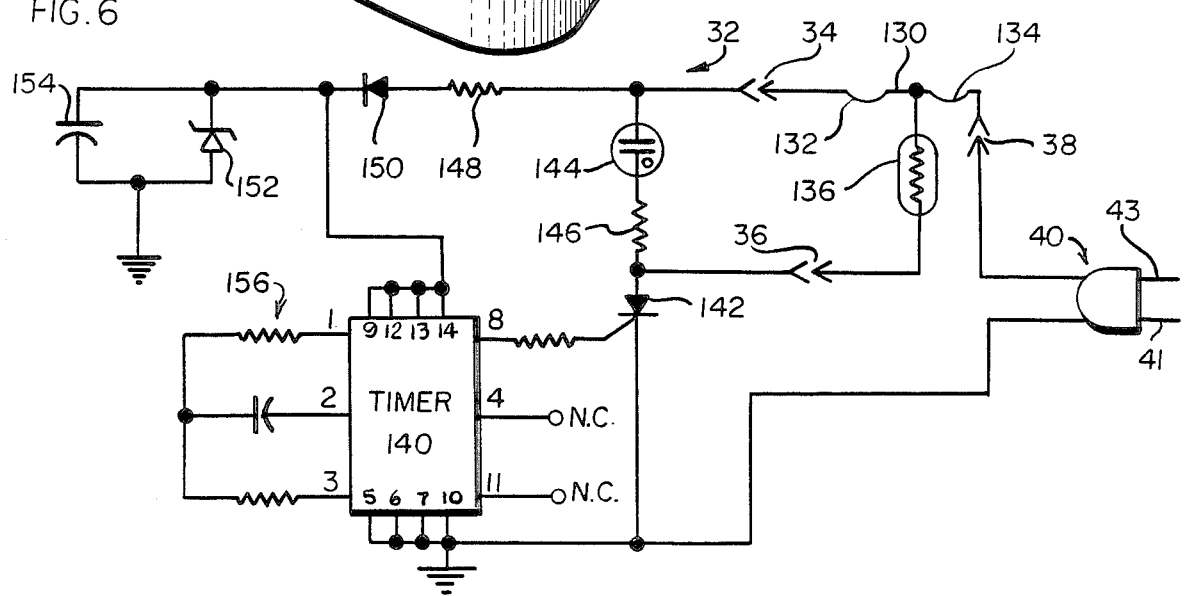
FIG. 6 is a schematic circuit diagram illustrating details of an energizing-and-timer circuit associated with a heating portion of the apparatus of the invention.

The circuit configuration of the circuit 32, including the heating element 136 and heat sink 130 is illustrated in FIG. 6, to which reference is now invited. Here, the heat sink 130 has been indicated in diagrammatic form, with the connections of the respective contactors 34 and 38 therewith being schematically indicated. The energizing-and-timer circuit comprises an electronic integrated circuit timer element 140, preferably of the type generally designated MC14541B. This timer is connected to the gate electrode of an SCR 142 which has its anode and cathode electrodes connected in series circuit with the heating element 136. Accordingly, when the timer module 140 coupled to the gate of SCR 142 permits current to flow from the anode to the cathode, this current will flow through the heating element 136 to heat the same and hence the heat sink 130 and the receptacles 18 and 20 for heating and disinfecting contact lenses therein. On the other hand, when the timer 140 "times out", the heating cycle will be discontinued by disabling the SCR at its gate electrode and ceasing current flow therethrough.

An additional indicator of the active/heating or inactive condition of the device is provided in the form of a small neon lamp element 144 connected in parallel circuit with heater 136, together with a suitable series-connected current limiting resistor 146. The timer is energized and begins timing upon connection of the AC connector 40 with an energized AC socket or receptacle. Suitable DC voltage and current levels to the timer or integrated circuit 140 are provided by way of a series current-limiting resistor 148, rectifying diode 150 and a simplified voltage regulating circuit consisting of a zener diode 152, preferably nine volts DC, and a parallel-circuit connected capacitor 154. The time in which the timer 140 times out and disables current flow through SCR 142 is determined by the selection of resistive and capacitive timing components as indicated generally at reference numeral 156.

While particular embodiments of the invention have been shown and described, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A contact lens disinfecting apparatus comprising: a housing including an upper housing part and a lower housing part; receptacle means defined in said upper housing part for receiving at least one contact lens and a quantity of liquid; heating means mounted in said housing and responsive to electrical energy for generating heat energy and configured and located for applying said heat energy to said receptacle means; electrical circuit means mounted in said lower housing part and coupled with said heating means for supplying electrical energy thereto; electrical connector means electrically coupled with said circuit and mounted to said housing for connection to mating electrical connector means for energizing said circuit means; and shield means interposed between said receptacle means and both said heater means and said electrical circuit means and defining collecting means and draining means for collecting and directing outwardly of the housing any liquid which may escape or otherwise occur beneath the receptacle means, so as to prevent said liquid from contacting either of said heater means or said electrical circuit means.

2. Apparatus according to claim 1 and further including cover means removably engageable with said housing for selectively covering said electrical connector means when said apparatus is not in use.

3. Apparatus according to claim 2 wherein said electrical connector means comprises a pair of AC blade-type contacts and wherein said cover means defines a pair of tubular receiving sheaths of a complementary form and configuration for surroundingly receiving said blade-type contacts.

4. Apparatus according to claim 2 wherein one of said housing parts includes a projecting lip portion and wherein said cover means further includes a resilient, manually releaseable, hook-like clip portion for releaseable engagement with said lip.

5. Apparatus according to claim 1 and further including a second shield member overlying said circuit means to further protect the same.

6. Apparatus according to claim 1 wherein said receptacle means comprises a pair of side-by-side, generally circular, dished receptacles and wherein said shield means comprises an oblong member defining a pair of complementary dished portions for underlying said receptacles, a raised peripheral rim and a downwardly extending drain portion in communication with the volume of said shield defined within said peripheral rim and in communication with the exterior of said housing for effecting drainage of liquid collected therefrom.

7. Apparatus according to claim 6 wherein said heating means comprises an oblong electrically conductive heat sink member of complementary form for underlying both said receptacles and a heating element mounted to a mid-portion of said heat sink; and wherein said electrical circuit means includes a first electrical contact engaged with said heating element and a pair of second electrical contacts engaged with respective sides of said heat sink underlying the two receptacles, one of said second pair of contacts also being electrically connected with the electrical connector means and the other of said second contacts being electrically coupled with said circuit means to energize the same; said shield means being interposed intermediate the underside of said receptacle means and said heat sink.

8. Apparatus according to claim 7 and further including a second shield member interposed intermediate said circuit means and said heating means.

9. Apparatus according to claim 1 wherein said housing includes an elongate assembly post extending between said upper and lower housing parts to effect assembly thereof and wherein said drain means includes an elongate, tubular drain member of greater transverse dimension than said assembly post and extending from said collecting means in surrounding relation to said post.

10. Apparatus according to claim 9 wherein one of said housing upper and lower parts has said assembly post integrally formed therewith and wherein the other said housing parts includes a through opening for receiving fastener means for engagement with said post, said through opening being of irregular shape and in communication with at least a portion of said tubular drain member to form an exit from the housing for liquid received therefrom.

11. A contact lens disinfecting apparatus comprising: a housing defining a pair of receptacles for receiving a pair of contact lenses and a quantity of liquid therein, heater means responsive to a predetermined electrical current for producing heat, said heater means being configured and positioned in said housing for radiating heat to said receptacles for disinfecting contact lenses therein, energizing-and-timing circuit means also mounted in said housing for controlling application of said predetermined electrical current to said heater means; AC connector means coupled with said housing for coupling with mating AC connector means for energizing said circuit means; and shield means interposed between said receptacle means and both the circuit means and said heater means and defining collecting means and draining means for respectively collecting and directing outwardly of the housing any liquid which may escape or otherwise exit beneath the receptacle means, so as to prevent said liquid from contacting said heater means or said electrical circuit means.

* * * * *